United States Patent [19]

Saxena

[11] Patent Number: 4,627,918
[45] Date of Patent: Dec. 9, 1986

[54] CHROMATOGRAPHY COLUMN USING HORIZONTAL FLOW

[75] Inventor: Vinit Saxena, Pinole, Calif.
[73] Assignee: Sepragen Corporation, Pinole, Calif.
[21] Appl. No.: 794,727
[22] Filed: Nov. 4, 1985
[51] Int. Cl.$^4$ .......................................... B01D 15/08
[52] U.S. Cl. ................................ 210/656; 210/198.2
[58] Field of Search ..................... 210/635, 656, 198.2

[56] References Cited

U.S. PATENT DOCUMENTS

| | | | |
|---|---|---|---|
| 3,230,167 | 1/1966 | Golay | 210/656 |
| 4,350,595 | 9/1982 | Gunkel | 210/198.2 |
| 4,496,461 | 1/1983 | Leeke et al. | 210/198.2 |

Primary Examiner—John Adee
Attorney, Agent, or Firm—Shyamala T. Rajender

[57] ABSTRACT

A method and apparatus for performing chromatographic separations utilizing horizontal flow through the separating medium bed are disclosed. The chromatographic separations may be carried out by using an apparatus involving a cylindrical column construction wherein the horizontal flow is in a radial direction as it passes through the separating medium bed or an apparatus involving a cubical column construction wherein the flow traverses from one end of the separating medium bed to the other end horizontally. The apparatus includes means for distributing the flow, achieving horizontal streamlines and collecting separated components. In one embodiment, the separating medium bed in adjustable in height.

32 Claims, 8 Drawing Figures

CHROMATOGRAPHY COLUMN USING HORIZONTAL FLOW

This invention relates to chromatography systems, particularly to an improved chromatography system utilizing horizontal flow through the separating medium, and more particularly to a method and apparatus for producing chromatographic separations utilizing horizontal flow through the medium.

BACKGROUND OF THE INVENTION

In a liquid chromatography system, a sample followed by an elution fluid are injected into a separation column. The separation column contains a packing or matrix medium or material, as well known in the art, which interacts with the various components of the sample fluid to be separated. The composition of the separating medium depends on the fluid being directed therethrough so as to produce the desired separation. The separation column generally known in the art are of a cylindrical construction and the fluid flows axially through a separating medium bed (packing or matrix) retained in the column. The medium bed is retained between supports or frits on either or both ends of the column. As the sample and elution fluids pass through the separating medium bed, the constituents of the sample fluid travel at different rates due to their interaction with the matrix or packing material. As a result, these constituents emerge separated (i.e., have different elution times) in the outlet stream of the column.

These prior known approaches are exemplified by the following U.S. Pat. Nos. 3,422,605 issued Jan. 21, 1969, to R. P. Crowley; 3,453,811 issued July 8, 1969, also to R. P. Crowley; 3,780,866 issued Dec. 25, 1973 to L. V. Ek et al; 4,133,562, issued Jan. 9, 1979 to L. H. Andren and 4,354,932 issued Aug. 19, 1982 to R. J. McNeil.

The available matrices or separation material beds for separating substances of large molecular weight are soft and compress easily. Matrix compression in turn causes dramatically reduced flow through the separation column. When chromatographic separation systems are scaled up for commercial purposes, more matrix volume is required and thus larger columns have to be employed. Additionally, the process requires a substantial increase in the fluid flow rate to achieve acceptable production rates. The combination of high flow rates and larger bed height (i.e., hydrostatic head) results in high pressure drops across the matrix that in turn further compress the matrix material, adversely affecting flow through the column. Some prior designs have addressed this problem by incorporating short, wide columns; i.e., columns with large cross-sectional area and reduced height. While this prior design does help reduce pressure drops and improve throughput, the geometry results in large saucer shaped (center dipping) columns when additional scale up is desired. Larger diameter columns have the problems of: (1) inconvenient geometry for fabrication, (2) difficulty in even packing of the column, (3) uneven distribution of the sample over the cross-sectional area, and (4) large dead volume leading to loss in chromatographic resolution. Due to these problems, scale up is often accomplished by using multiple columns in parallel or using larger columns but with smaller diameter-to-height ratios. The first alternative mentioned above can be cumbersome and often results in high costs while the second alternative leads to a recurrence of the problem with compression of the matrix or separator material bed. The process has to be reoptimized since the flow rates have to be altered to reduce pressure drop, leading to considerable expense in terms of time and material. Thus, a need exists in the art for an approach which enables scaling up of chromatographic systems while overcoming the problems enumerated above.

Therefore, it is an object of the present invention to provide a method and apparatus for chromatographic separation which overcomes or significantly reduces prior known problems associated with larger diameter columns, at the same time, lending itself to scale up dimensions.

A further object of the invention is to provide a chromatographic separation system which includes means for reducing the pressure drop across the separation material bed or packing in the direction of flow.

A still further object is to provide a method and apparatus for maintaining an even bed height across the cross-section of a separation material bed of a chromatographic column, while maintaining an even distribution of the sample material across the bed.

Another object of the invention is to provide a chromatographic column which has a geometry for convenient assembly and ease of packing, while enabling a scale-up thereof.

Another object of the invention is to provide a chromatography column utilizing horizontal flow of the sample material through the matrix of the separating medium.

Another object of the invention is to provide a chromatographic column utilizing a cylindrical or cubical construction wherein the flow of the sample material and elution fluid is horizontal (radial flow direction) through the matrix.

Still another object of the invention is to provide an apparatus and method for performing chromatographic separations utilizing horizontal flow through the separating medium bed while maintaining even distribution of the flow and minimal pressure drop across the bed.

Another object of the invention is to provide a chromatographic column having an adjustable bed height.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

SUMMARY OF THE INVENTION

To achieve the foregoing and other objects and in accordance with the purpose of the present invention as embodied and broadly described herein, the present invention is directed to an apparatus and a method for performing chromatography in a horizontal mode with appropriate column configuration. This may be accomplished by means of a chromatographic column constructed so as to have an inner and outer annuli, with the matrix material being packed therebetween. The bed height is thus computed as the distance between the inner and outer annuli. Chromatography consequently takes place radially in the column. Furthermore, horizontal flow may also be achieved in a cubic arrangement where the flow takes place between two vertically held end plates.

In each of the above two configurations, the hydrostatic head does not contribute to the pressure drop, resulting in lower pressures and lower bed compression for the same bed height, as compared to the vertical flow systems. The column configurations of the present invention result in even bed height since the inlet and outlet distributors are fixed. Uneven bed contraction or expansion will thus affect the cross-sectional area but not the effective bed height. The distributor and collection channels are designed to provide even application of the sample and horizontal streamlines across the chromatographic bed. The long, vertical column assembly with horizontal flow is easy to fabricate and convenient for packing and handling. Furthermore, since the bed height is constant along the length of the column, both the cross-sectional area and bed volume are proportional to the column length. Thus, scale-up is possible by linearly increasing the length of the column in proportion to the desired scale of operation. At any scale of operation, the pressure drop remains constant and scale up is accomplished easily by linear increments of the column bed length. In one embodiment, means are provided to make the height of the column adjustable while retaining the horizontal flow path.

The method of this invention may be carried out by two different column configurations or construction, one cylindrical and the other, cubical, each utilizing horizontal fluid movement (both sample and carrier medium or eluant). In the cylindrical construction, the horizontal flow is in a radial configuration or direction, the flow being from the outer periphery of the separating medium bed and through the bed in a radially inwardly direction, or vice versa. In the cubical construction, the flow traverses horizontally from one end to the other end of the separating medium bed.

DETAILED DESCRIPTION OF THE INVENTION

The present invention involves a chromatography column utilizing horizontal flow of the sample and carrier medium or eluant material. The column may be of a cylindrical construction or of a cubical construction, with the flow of a sample fluid through a separating medium bed therein being in a horizontal direction. The column of this invention includes means for evenly distributing the flow, achieving horizontal streamlines, and collecting the separated components, while providing easy scale-up thereof for high volume operation.

Figure 1:
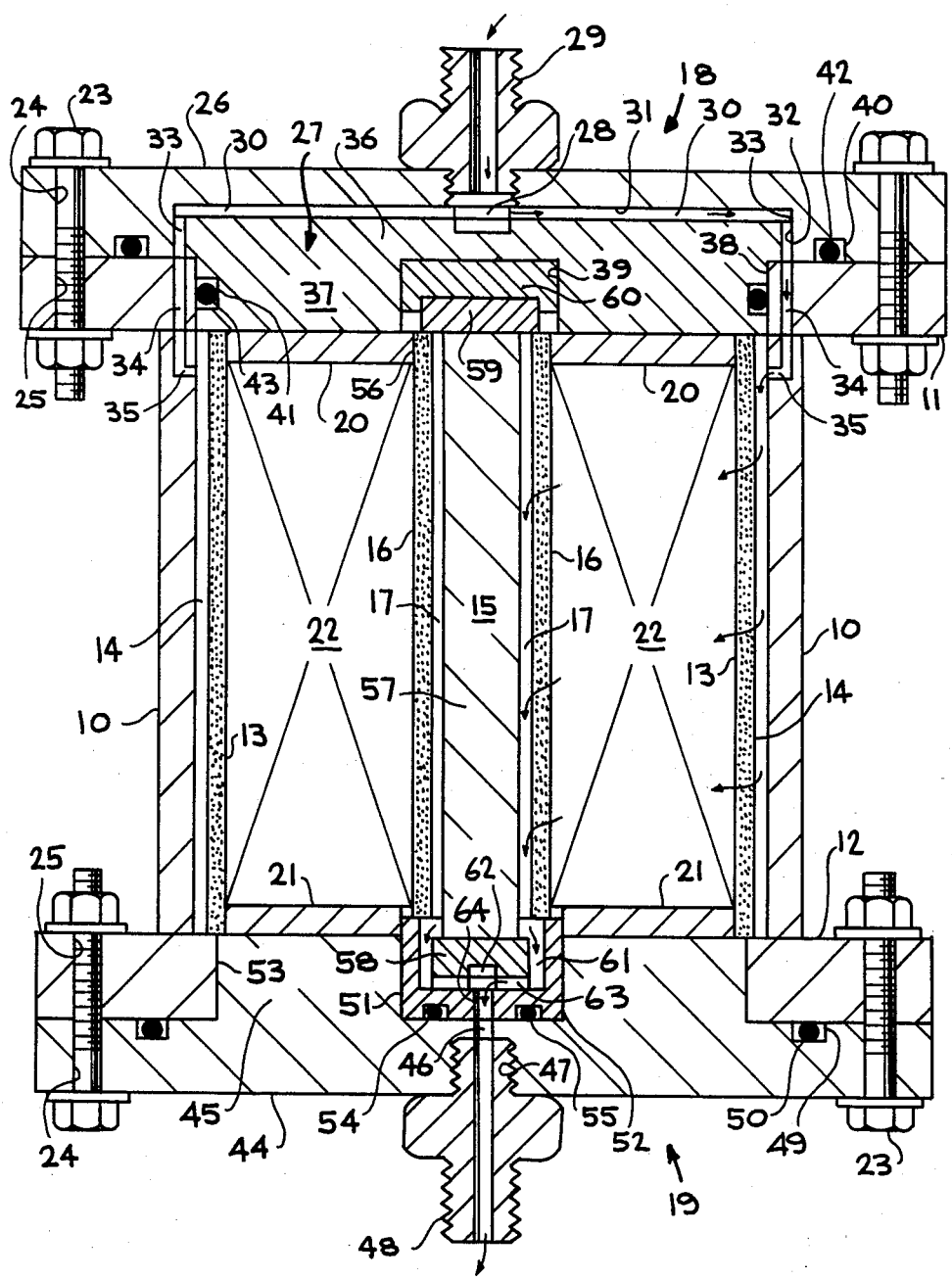
FIG. 1 is a cross-sectional view of an embodiment of a chromatographic column of cylindrical construction utilizing horizontal flow in accordance with the subject invention.
Figure 2:
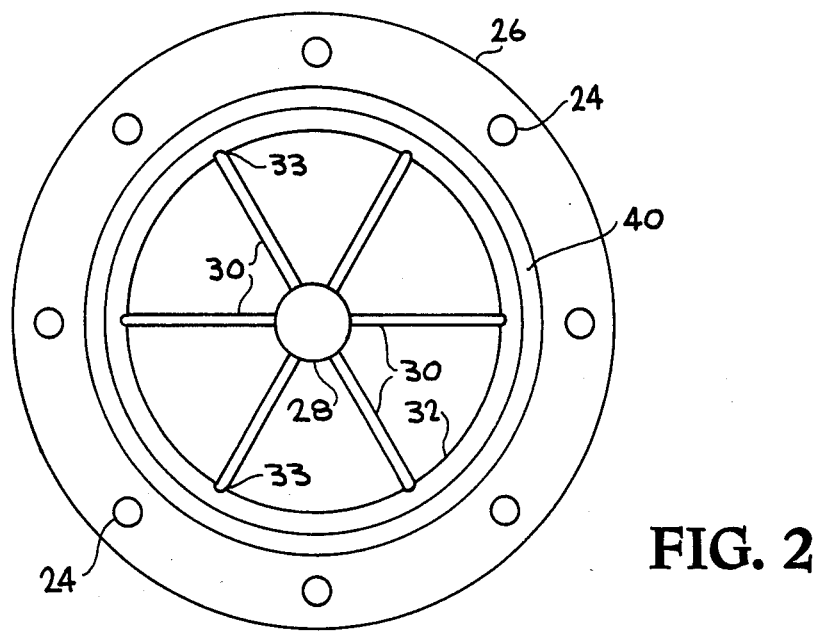
FIG. 2 is a view of the end cap or member of the apparatus depicted in FIG. 1, illustrating the spaced inlet flow distributor channels.
Figure 4:
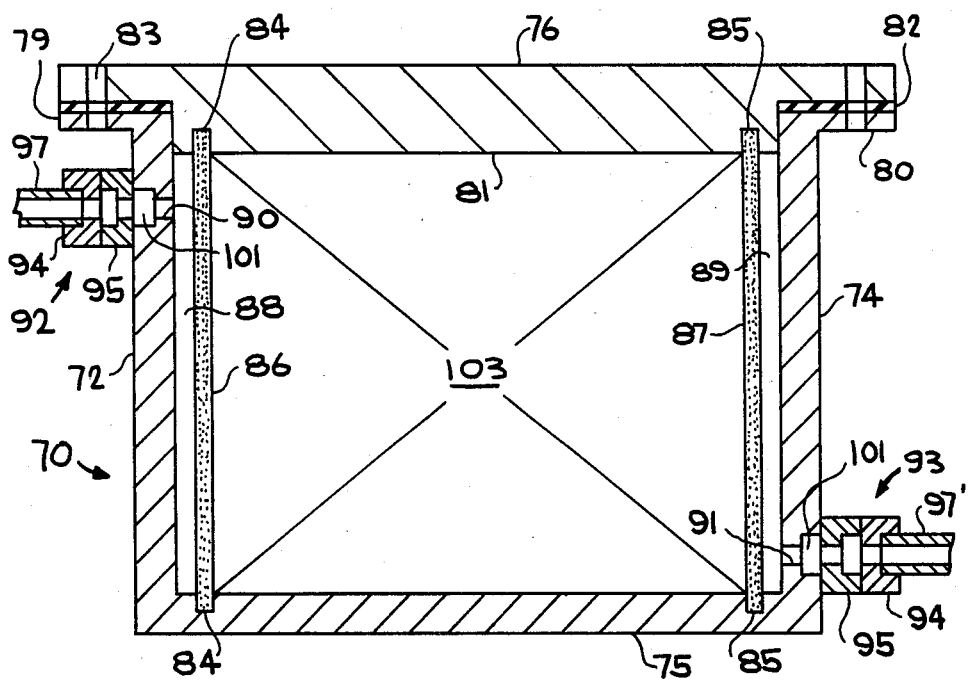
FIG. 4 is a cross-sectional view of an embodiment of a chromatographic column of cubical construction utilizing horizontal flow in accordance with the invention.
Figure 3A:
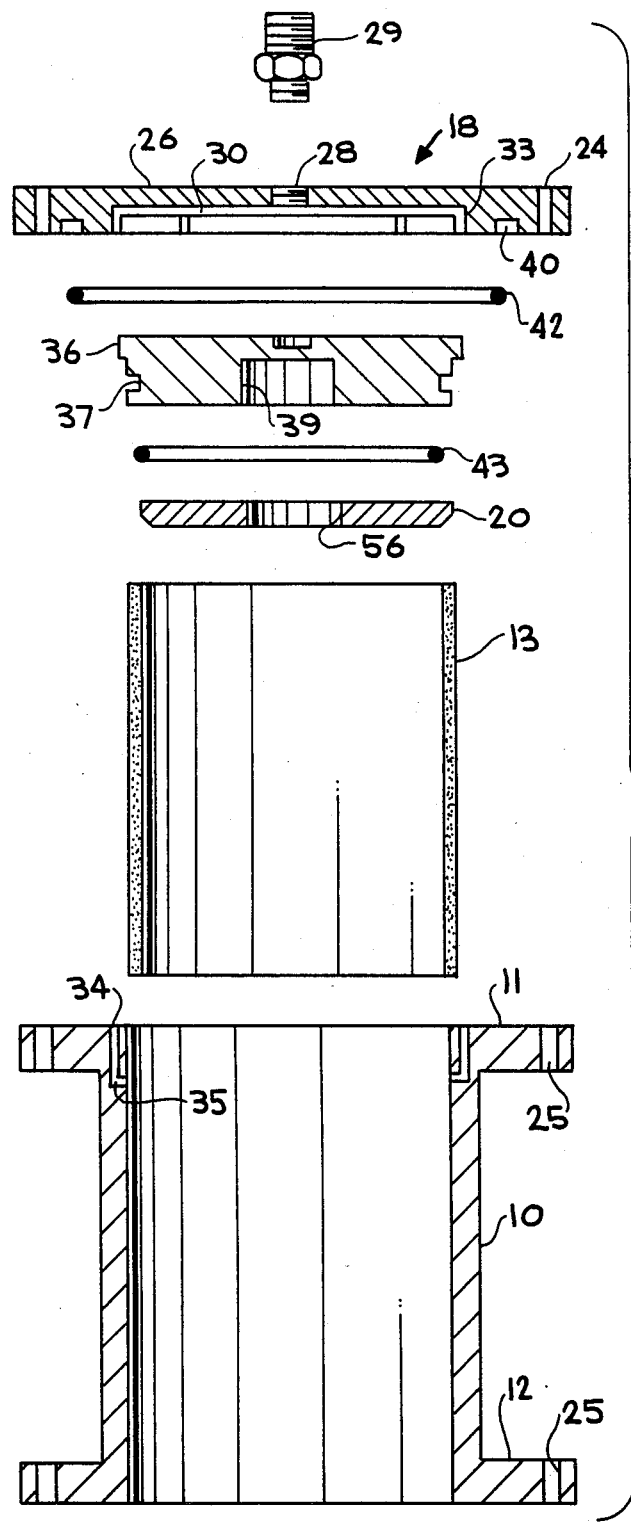
FIG. 3 is an exploded view of the chromatographic column of FIG. 1.
Figure 3B:
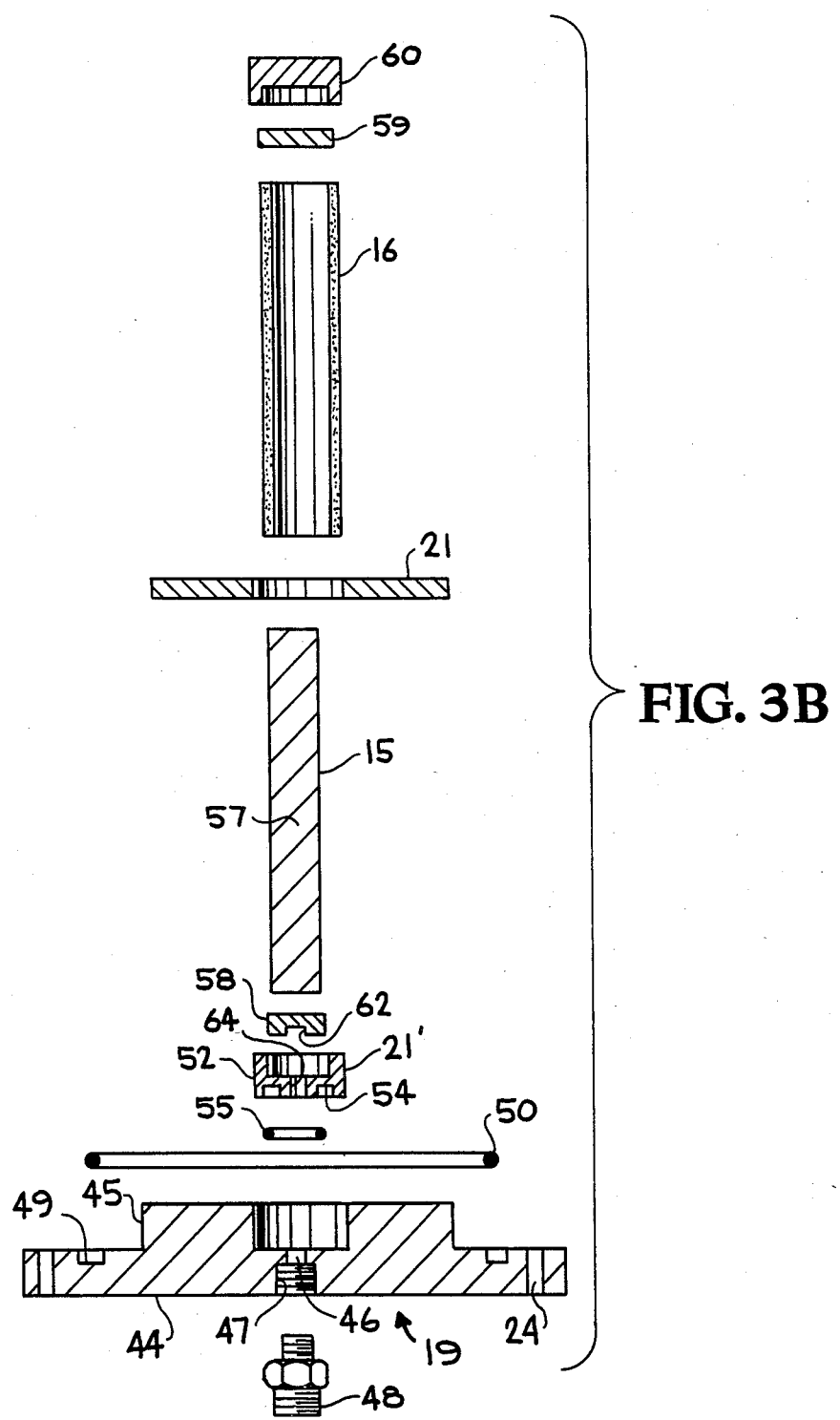
Figure 5:
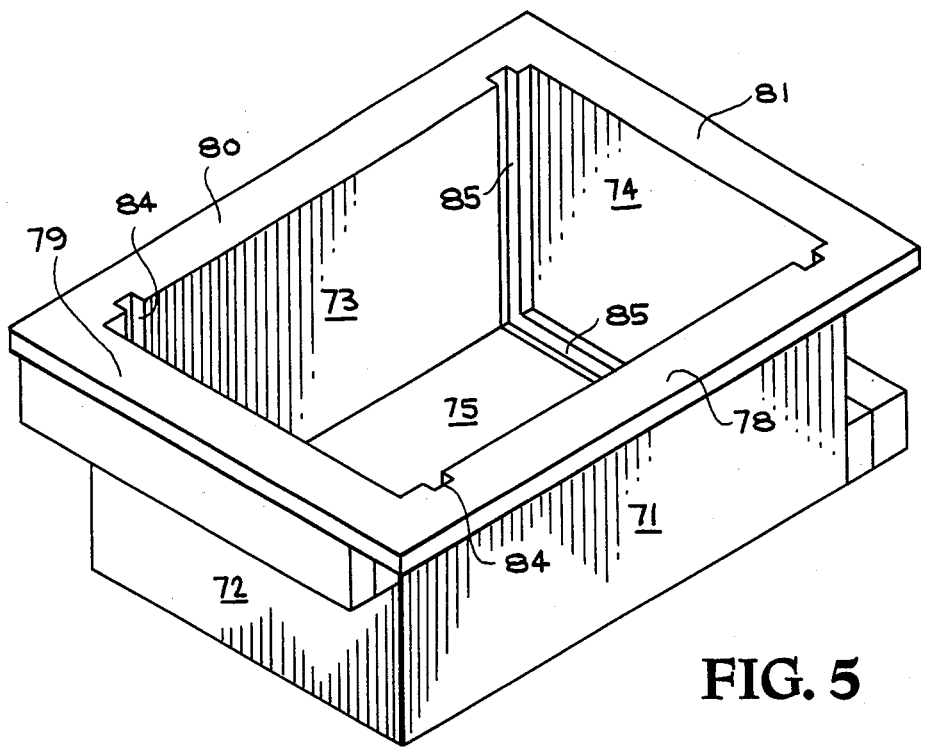
FIG. 5 is a partial view of the chromatographic column of FIG. 4.

The column of this invention overcomes the problems associated with large diameter or length columns by: (1) providing a convenient geometry for fabrication; (2) ease of packing the column with separating medium; (3) even distribution of the sample matrix over the separating medium bed; and (4) no dead volume area. The column bed height of the cylindrical embodiment is given by the distance between inner and outer annuli, and thus can be scaled-up by increasing the length linearly, without any increase in pressure drop across the separating material bed. FIGS. 1-3 illustrate an embodiment of the subject chromatography column having a cylindrical configuration, while FIGS. 4 and 5 illustrate an embodiment having a cubical configuration. Each embodiment utilizes a horizontal fluid flow of the sample and the elution fluids through or across the separating medium bed, matrix, or packing retained within the column. Each embodiment utilizes a distribution system for the sample fluid which evenly distributes the sample fluid with respect to the bed, matrix or packing.

Referring now to the embodiment of a cylindrically constructed chromatography column illustrated in FIGS. 1-3, the column basically comprises a cylindrical outer wall, housing or casing 10 having outwardly extending flanges 11 and 12 secured at opposite ends, a porous tubular frit 13 located within said outer wall and spaced therefrom to define an annular channel or passage 14 therebetween, a cylindrical core or member 15 and a porous tubular frit 16 located centrally within outer wall 10 and spaced from one another to define an annular channel or passage 17 therebetween, an inlet end plate cap or member generally indicated at 18, an outlet end plate cap or member generally indicated at 19, a pair of collar-like members 20 and 21 located at opposite ends of core 15, flange 21 including a central cup-like section 21′, and a bed, package, or matrix 22 of selected separating material or medium retained between frits 13 and 16 and between collar-like members 20 and 21, with the end caps or members 18 and 19 being secured to flanges 11 and 12, respectively, by bolts or other securing means 23, eight(8) in this embodiment, which extend through openings 24 and 25 in end caps 18 and 19 and flange 11, respectively. The porous frits 13 and 16 are coaxial with respect to each other and have a permeability substantially identical to the separating or chromatographic packing material 22 for separating the components of a sample fluid passing therethrough.

Inlet end cap or plate 18 comprises an outer plate or member 26 and an inner plug or member generally indicated at 27, members 26 and 27 being provided with a centrally located threaded opening 28 into which a threaded coupling 29 is secured and to which is connected a supply (not shown) of sample material or fluid to be separated. Outer plate or member 26 is provided with a plurality of fluid distribution grooves or channels 30 (see FIG. 2) each terminating at one end at threaded opening 28 and extending radially outwardly along an inner surface 31 of outer plate 26 to a lip section 32 of outer plate 26 which is provided with a plurality of matching or corresponding grooves or channels 33 which match or align with a plurality of openings or passages 34 in flange 11, and which in turn align with a plurality of L-shaped openings or passages 35 in outer wall or casing 10. Thus, sample material or fluid from an external supply passes through coupling 29 into opening 28 and is evenly distributed into annular channel 14 via said plurality of grooves 30, grooves 33, openings 34 and L-shaped openings 35. In the embodiment illustrated in FIGS. 1–3, the fluid distribution is carried out by six (6) grooves 30 and 33 and corresponding openings 34 and 35, spaced 60° apart around the threaded opening 28 and annular channel 14. The number of fluid distribution grooves or channels may be increased or decreased with the purpose thereof to provide an even distribution of the sample fluid around the frit 13 and packaging or chromatography material 22. While the grooves or channels 30 and 33 are illustrated as being on surface 31 and lip section 32 of outer plate 26, the grooves may extend along the adjacent or matching surface of inner plug or member 27 or both.

Inner plug or member 27 of inlet end cap 18 includes two sections 36 and 37 with different diameters, section 36 extending over an inner portion of flange 11 and terminating adjacent opening 34, with section 37 extending into an opening 38 in flange 11. Section 37 of plug 27 is provided with a centrally located chamber or countersink 39 into which one end of the cylindrical core 15 extends.

To prevent leakage, outer plate 26 is provided with an annular groove 40 and section 37 of inner plug 27 is provided with an annular groove 41 into which are positioned seals 42 and 43, respectively, such as O-rings, which cooperate with adjacent surfaces of flange 11 to form a fluid seal therebetween.

Outlet end cap or plate 19 includes an outlet plate section 44 and an inner plug section 45, plug 45 being of a smaller diameter than plate 44. Outer plate section 44 is provided with openings 24, eight in this embodiment for bolts 23, and with a central opening 46 having an enlarged threaded section 47 into which a coupling 48 is secured. Coupling 48 is adapted to be connected to a point of use or receiver, not shown, to collect the sample fluid components being discharged from the column, as described hereinafter. Outer plate section 44 also includes an annular groove 49 for retaining a seal 50, such as an O-ring, in a sealing relation with flange 12. Inner plug section 45 of end cap 19 is provided with a central opening 51 in alignment with opening 46 of outer plate section 44 and is adapted to receive a central section 52 of flange 21 and an end of cylindrical core 15. Inner plug section 45 extends into an annular opening 53 of flange 12, while outer plate section 44 extends along flange 12 and is secured thereto by bolts 23. Central section 52 located within flange 21 is provided with a groove 54 containing a seal 55, such as an O-ring, which abuts against an inner surface of outer plate section 44 to form a fluid seal therebetween.

Flange 20 is provided with a central opening 56 through which extend cylinder 15 and frit 16. Flanges 20 and 21 function, in cooperation with frits 13 and 16, to retain the separation or chromatography material 22. By way of example, the porous frits 13 and 16 may be constructed of polyethylene, teflon, or polypropylene and the like, and the material 22 may be composed of or selected from materials commonly known and used in chromatography and include but not limited to cross-linked agarose, polyacrylamide, or cellulose and the like. For a sample fluid consisting of proteins for example, the frits 13 and 16 would be constructed out of polyethylene, having a porosity in the range of from about 30 to 60 microns, and the material 22 would be composed of 200 to 400 mesh agarose or cellulose having a permeability substantially the same as the material of the frits 13 and 16.

Cylindrical core 15, in addition to functioning as a support for porous frit 16 and for defining the flow channel 17, serves as an exhaust or discharge distributor as the components of the sample fluid pass through frit 16 into the annular channel 17. The core 15, as illustrated, is of solid construction, but could, if desired, include hollow components, the components consisting of a body member 57, a pair of end pieces or members 58 and 59 secured to body member 57, and an end cap 60 secured to end member 59. End pieces or members 58 and 59 are larger in diameter than body member 57 but smaller in diameter than end cap 60. End cap 60 is constructed so as to have a slip fit within the chamber 39 of inner section 37 of inner plug or member 27. End piece or member 58 is positioned in a snug or slide fitting relation in the central section 52 of flange 21. End member 58 is provided with a plurality (four in this embodiment) of spaced grooves or channels 61 along the edge surface thereof. The outer end surfaces of end member 58 is provided with a central chamber or countersink 62 and a plurality (four in this embodiment) of radially extending grooves or channels 63 terminating in chamber 62 and grooves 61, chamber 62 being aligned with a central opening 64 in central section 52 of flange 21, which in turn is aligned with opening 46 in outer plate 44 of end cap 12. Thus, the annular channel 17, grooves 61, grooves 63, chamber 62, opening 64, opening 46, and coupling 48 form an outlet fluid distribution arrangement for discharging fluid components from the separation or chromatographic column. If desired, the grooves or channels 61 and 63 may be formed in the inner side and end surfaces of the central section 52 of flange 21 located adjacent end piece or member 58.

In the operation of the apparatus of the instant invention as embodied in FIGS. 1–3, the sample fluid to be chromatographically separated either by itself or in a carrier medium followed by a suitable eluant, as known in the art, are directed through coupling 29, chamber 28, grooves 30 and 33, openings or passages 34 and 35 into the annular channel 14 surrounding porous frit 13, which then flows down and fills the channel or annulus 14. The sample fluid diffuses through the porous frit and flows horizontally in a radial direction through the packing or bed 22 of the separating chromatographic material. The separation of the components in the sample fluid takes place as it passes through the bed of material 22 as known in the art. The separated components diffuse radially inward through the frit 16 and into the annulus or channel 17, and flow vertically down channel 17 and through the four grooves or channels 61 and 63 into chamber 62 of cylindrical core 15, and emerge from the apparatus via openings 64 and 46 and coupling 48, whereby the separated sample fluid components are directed to appropriate containers, point of use and the like.

While the embodiment shown in FIGS. 1–3 illustrates the horizontal flow along a radially inward direction, it should be recognized that the cylindrical arrangement can be modified to direct the horizontal flow along a radially outward direction. Such an arrangement would require modification of the fluid inlet distributor and the fluid component collection assembly. The principle underlying the subject invention is that the flow through the chromatography bed is in a horizontal direction which overcomes the problems associated with vertical passage of the fluid through the bed, as discussed earlier.

For the fluid streamlines through the bed material 22 to be truly horizontal, the axial pressure drops in both annular channels 14 and 17 should be the same. Since the flow rate is the same through porous frits 13 and 16, this condition can be achieved by having the same cross-sectional areas in both channels 14 and 17. Thus, if the inner diameter of the cylindrical outer wall 10 is R, and the width of gap or annulus or channel 14 is t, and if the cylindrical core 15 has a diameter r, the width of gap or channel 17, t' may be calculated by equating the two cross-sectional areas such that:

$$t' = \frac{R^2}{2}\left(\frac{2t}{R} - 1\right) \quad (1)$$

Using this design criterion, a horizontal flow path with minimal short-circuiting of the sample fluid is achieved.

While the components 10, 13, 15 and 16 of the embodiments shown in FIGS. 1–3 have been illustrated and described as being cylindrical, other configurations, such as square, hexagonal, or octagonal, may be used. It is understood that the number and spacing of the inlet fluid distributor channels or grooves may be changed depending on the configuration of the chromatographic column. Furthermore, the column of FIG. 1 can also be modified by replacing the fluid flow distributor arrangement in end cap 18 with an external fluid distributor with lines which are directly connected to the openings or passages 35 in outer wall 10. In such a case, the L-shaped openings 35 would be replaced with openings that extend through the outer wall 10 for attachment to fluid distributor lines.

Figure 6:
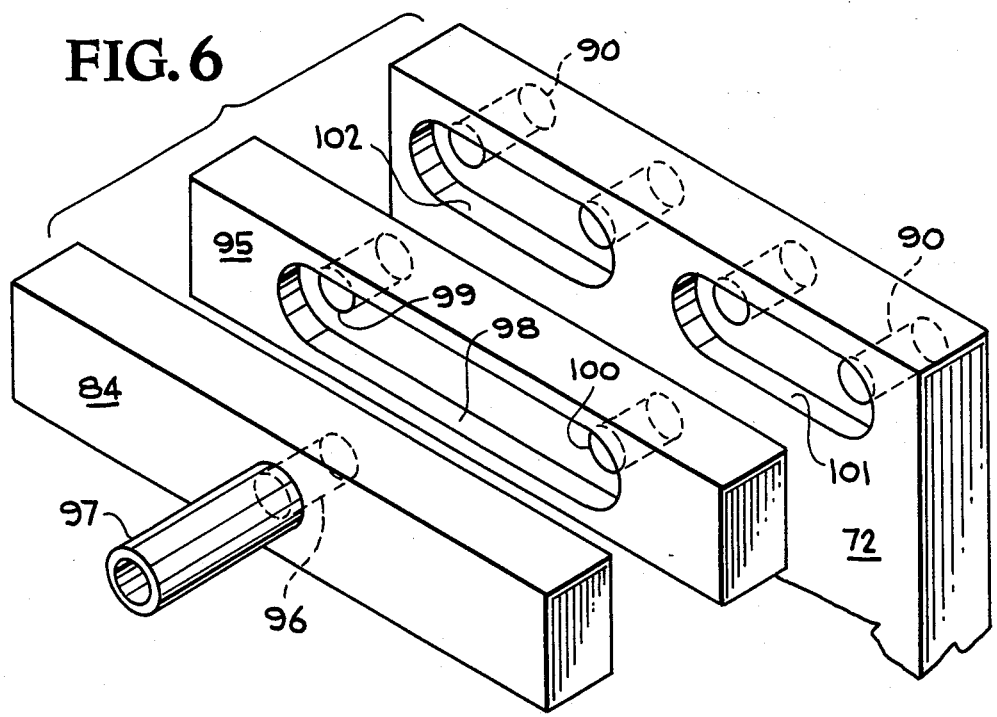
FIG. 6 is an exploded view of the fluid manifold of the FIG. 4 embodiment.

The embodiment of the invention illustrated in FIGS. 4–6 is of a cubical construction utilizing the principle of horizontal flow chromatography. Basically, the column structure is of a box-like construction with flow channels located at opposite ends with fluid distribution or manifolds located externally of the box and secured to each flow channel. Thus, a sample fluid to be separated flows through an inlet manifold into a first flow channel formed between a wall of the box and a porous frit, through the frit, through a separation medium bed, through a second porous frit into a second fluid channel formed by the second frit and an opposite wall of the box, and exits through an outlet channel. The flow across the separation medium bed is in a horizontal direction as in the embodiment of FIGS. 1–3.

Referring now to FIGS. 4–6, the cubically constructed embodiment comprises a box, housing or casing, generally indicated at 70, comprising four walls or sides 71, 72, 73 and 74, a bottom or end section 75, and a top or end section lid 76. Each of the walls 71–74 is provided with an upper flange 77, 78, 79 and 80, which may be integral or secured to the respective wall. The lid 76 includes an inner portion 81 with a reduced cross-section, configured to tightly fit into the upper sections of the walls. A gasket or seal 82 is located between the lid and wall flanges. As shown in FIG. 4, the lid 76, gasket 82, and wall flanges 77–80 are provided with a plurality of apertures or openings 83 for bolts or other securing members. As seen in FIGS. 4 and 5, walls or sides 71 and 73, bottom 75 and inner portion 81 of lid 76 are provided with a pair of aligning grooves 84 and 85 into which a pair of porous frits 86 and 87 in sheet form are positioned, and form a pair of fluid flow channels 88 and 89 between the frits and the associated walls. Walls 72 and 79 are provided with a plurality of spaced apertures or openings 90 and 91, only one shown in each wall, to which are connected an inlet fluid distributor or manifold 92 and an outlet fluid collection distributor or manifold 93, as shown in FIGS. 4 and 6. The fluid manifolds 92 and 93 are similarly constructed but operate in reverse directions. As shown more clearly in FIG. 6, each manifold comprises a pair of elongated strips or members 94 and 95. Strip 94 has a single centrally located aperture 96 therein to which is connected a sample and eluant fluid inlet supply line or tube 97, manifold 93 provided with an outlet or discharge line or tube 97'. Strip 95 is provided with an elongated groove or slot 98 which has a pair of apertures 99 and 100 located in the outer portion of the slot. The walls 72 and 74 of box 70 are each provided with a pair of spaced slots 101 and 102, which have associated apertures 90 or 91 located at the outer end of the slots 101 and 102. FIG. 6 illustrates the inlet manifold 92 mounted with respect to spaced apertures 90 in wall 72, with the understanding that wall 74 is constructed similarly to include a pair of spaced slots positioned relative to the aperture 91 and the fluid outlet manifold 93 as seen in FIG. 4. The slots 90 and 91 are located in spaced relation across their respective walls to provide uniform fluid distribution into inlet channel 88 and uniform fluid component discharge or exhaust from collector channel 89. The strips or members 94 and 95 may, for example, be glued together or held together by other means. As discussed above with respect to the embodiment illustrated in FIGS. 1–3, the areas of the respective fluid channels are designed to establish the desired pressure drop to enable horizontal flow across a bed 103 of chromatographic material or medium located intermediate porous frits 86 and 87. Note that the height and width of both flow channels 88 and 89 are the same. The permeability of the material of bed 103 and the porous frits 86 and 87 are also substantially identical. The manifold arrangement illustrated in FIG. 6, insures that all four substreams of sample fluid directed into fluid channel 88 travel the same distance and thus provide even distribution across the bed 103. Similarly, the collection or outlet manifold provides even collection of the sample fluid components.

The cubical embodiment illustrated in FIGS. 4–6 is not intended to be limiting, as other configurations may be used. Additionally, the grooves in the lid and the bottom of the box may be omitted, with the frits being retained by the grooves in the two walls and by the pressure exerted on the frits by the lid and the bottom of the box. Furthermore, while the manifolds have been shown in FIG. 4 as being spaced from the lid and bottom of the box, they may be located as shown in FIG. 5 abutting the lid and the bottom of the box. Additionally, the gasket shown in FIG. 4 may be replaced by an O-ring seal and the lid or wall flanges provided with appropriate grooves for retaining the same as known in the art. In the embodiment illustrated in FIGS. 4–6, the walls and bottom of the box may be secured together by any suitable means which include but not limited to screws, glue or any appropriate bonding material. Similarly, the strips or members of the manifolds may be retained together and held on the walls of the box by any suitable means such as glue, screws or other bonding material. The inlet and outlet manifolds may be replaced with other fluid distributing means.

Figure 7:
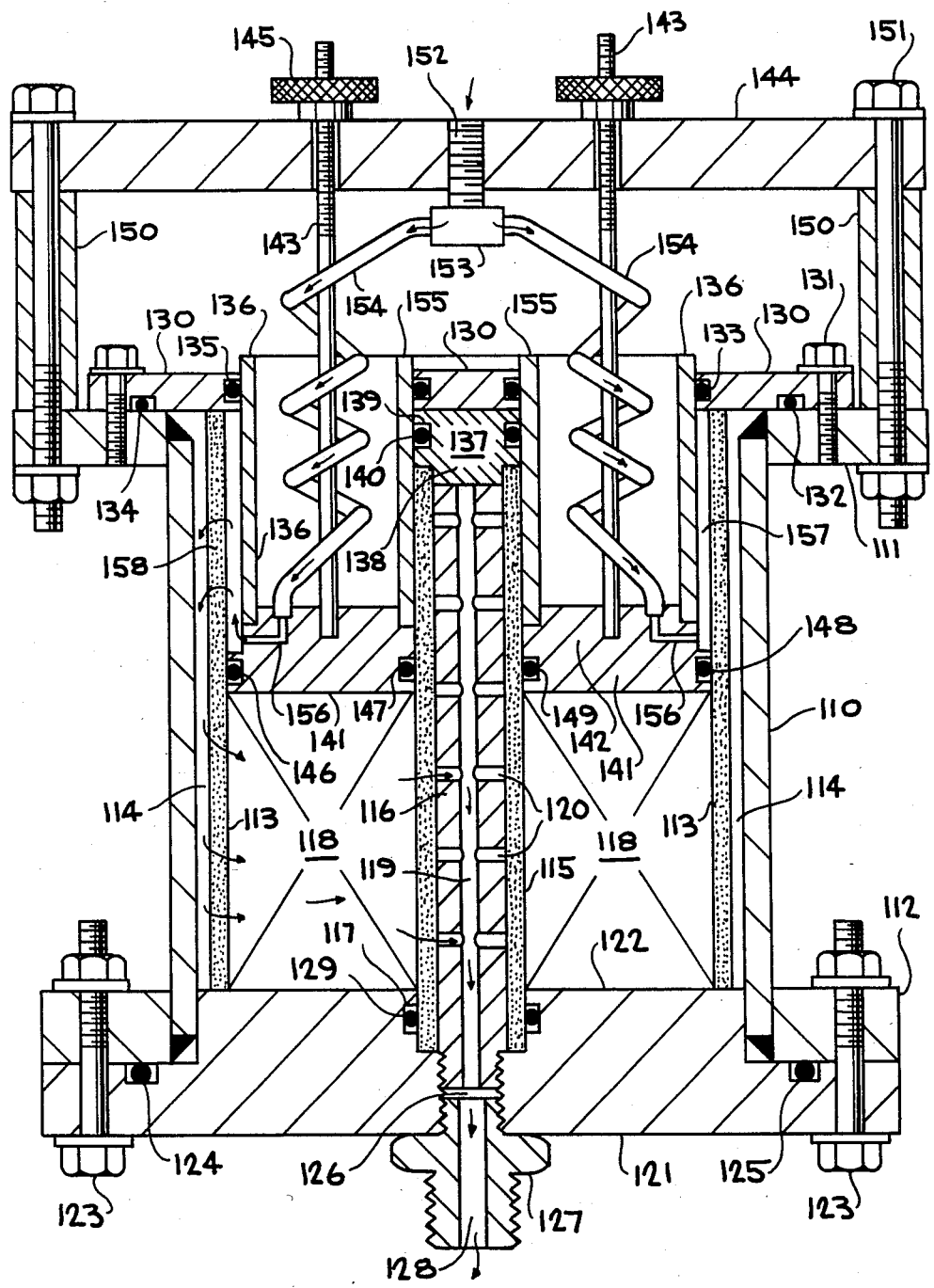
FIG. 7 illustrates an embodiment of the invention which incorporates an adjustable height bed.

The FIG. 7 embodiment is of a cylindrical type, similar to the embodiment of FIGS. 1–3, but includes an adjustable height chromatographic column. The column of FIG. 7 is cylindrical in configuration, and is illustrated with a reduced column height. In actual practice, the column can be operated at a reduced height or at full column height. As is readily apparent, the adjustable height column of the apparatus depicted in FIG. 7 utilizes a modified, fluid inlet manifold or distributor and a modified fluid component collector arrangement, compared to the embodiment shown in FIGS. 1–3.

Referring now to the embodiment shown in FIG. 7, the chromatographic column includes a housing or casing 110 having outwardly extending end flanges 111 and 112, secured together such as by welding. A first porous frit 113 is located within housing 110 to define an annular inlet fluid channel 114 therebetween. A second porous frit 115 is positioned in spaced relation with the first frit 113 and closely adjacent to a core or member 116. A quantity of chromatographic separation material forms a bed 118 located intermediate the frits 113 and 115. The core 116 includes a longitudinally extending fluid passage or opening 119 and a plurality of fluid passages or openings 120 transverse to opening 119 which forms a fluid component collection channel. A lower end cap or plate 121 having section 122 of a reduced diameter is secured to flange 112 of housing 110 by bolts 123 which extend through openings in the end cap 121 and flange 112. Section 122 of end cap 121 is constructed to fit snuggly within housing 110. A groove 124 is formed in end cap 121 to retain a seal 125, such as an O-ring, between flanges 112 and end cap 121. End cap 121 is provided with a central opening 126 having sections of different diameters, one section of opening 126 being constructed to receive one end of frit 115 and one end of core 116, while another section of opening 126 is threaded to provide attachment to a coupling 127 having a fluid passage 128 therethrough for connection to a fluid component collection arrangement, not shown. A groove is formed in section 122 of end cap 121 to retain a seal 129, such as an O-ring, between frit 115 and section 122.

Frit 113 is retained in housing 110 by a plate or member 130 secured to flange 111, such as by screws 113. Plate 130 is provided with a pair of grooves 132 and 133 for retaining seals 134 and 135, such as O-rings, between plate 130 and flange 111 and between plate 130 and a movable casing or tube 136. Core 116 includes an end member 137 having a section 138 of reduced diameter and a groove 139. Section 138 of reduced diameter extends into an end of and provides support for frit 115, while groove 139 retains a seal 140, such as an O-ring, which cooperates with casing or tube 136. The end member 137 is retained by plate 130.

Tube 136 is secured at one end to an end cover or plate 141 having a section 142 of reduced diameter which extends into tube 136. End cover 141 is constructed to include a central opening in which frit 115 and core 116 are located and is adapted to be raised and lowered by a plurality of rods or members 143 which extend through an upper end cap 144 and to which adjustable knobs or wheels 145 are threadedly attached. It can be readily seen that as end cover 141 is raised or lowered, the height of the bed 118 is correspondingly increased or decreased. End cover 141 is provided with grooves 146 and 147 which retain seals 148 and 149, such as O-rings, which cooperate respectively with frits 113 and 115, to prevent fluid leakage between the end cover 141 and frits 113 and 115.

End cap 144 is secured to flange 111 via a plurality of spacers 150 and bolts 151, only two of which are shown. End cap 144 is provided with a central opening 152, which is threaded to connect to a housing 153 forming a fluid distributor and to a coupling, not shown, for connection to a fluid supply or source. Connected to fluid distributor or housing 153 are a plurality of flexible tubes or conduits 154 (two shown but six utilized in this embodiment), flexible tubes or conduits 154 being located within the movable casing or tube 136. One end of each of the flexible tubes 154 is secured to an L-shaped passage way 156 in end cover or plate 141. An inner tube 155 is positioned around core 116 and secured to plate or end cover 141. End cover 141 is provided with an outer cut-away section 157 in which passage ways 156 terminate. The outer cut-away section 157 of end cover 141 is in fluid communication with an annular space 158 between tubes 136 and frit 113.

By way of example, with six (6) flexible tubes 154 located in equal spaced relation around end cover 141 within the housing 110, sample fluid to be separated in chromatographic bed 118 is supplied through opening 152 into distributor housing 153. An shown by flow arrows, the fluid directed into distributor 153 is equally channelled through the plurality of flexible tubes 154, L-shaped passageways 156, cut-away section 157 into annular space 158. The fluid then passes through porous frit 113 into inlet fluid channel 114. From channel 114 the fluid passes back through porous frit 113 horizontally through bed 118 and the fluid components then pass through porous frit 115, whereafter the fluid components are directed through openings 120 into opening 119 of core 116 and out through opening 126 in end cap 121 to a collection or use point. Here, as in the embodiment shown in FIGS. 1–3, the fluid passes horizontally through the chromatographic material bed 118 for the reasons described above.

By adjustment of the wheels or knobs 145, the end cover 141 is raised or lowered which adjusts the volume or height of the bed 118, while maintaining even distribution of the fluid around the periphery and through the bed, and even and uniform collection of the fluid components.

While the embodiment of FIG. 7 has been illustrated and described as being cylindrical in configuration, other configurations such as cubical, hexagonal, and octagonal, may be utilized.

It has thus been shown that the present invention provides a chromatography column utilizing horizontal flows through the separating medium bed, overcoming the problems associated with large diameter columns, while enabling scale-up to accommodate the demand for high volume, high resolution fluid separation. Thus, the present invention provides a substantial advance in the state of this art.

The foregoing description of the preferred embodiments of the subject invention have been presented for purposes of illustration and description and for a better understanding of the invention. It is not intended to be exhaustive or to limit the invention to the precise form disclosed; and obviously, many modifications and variations are possible in light of the above teaching. The particular embodiments were chosen and described in some detail to best explain the principles of the invention and its practical application to thereby enable others skilled in the relevant art to best utilize the invention in various embodiments and with various modifications as are suited to the particular use contemplated. It is intended that the invention be defined by the claims appended hereto.

What is claimed is:

1. A chromatography column utilizing horizontal flow of sample material passing therethrough comprising:
   a housing defining a chamber therein and including at least one removable end section,
   a pair of longitudinally extending porous frits positioned in spaced relation within said chamber of said housing,
   a bed of chromatographic separation material positioned in said chamber of said housing and intermediate said porous frits,
   one of said porous frits being spaced from said housing to define an inlet channel therebetween,
   another of said porous frits being positioned to define an outlet channel,
   distribution means operatively connected to said inlet channel,
   collector means operatively connected to said outlet channel,
   said distribution means and said inlet channel being constructed to direct associated material to be separated in said bed evenly across a longitudinal length of said bed in a substantially horizontal direction.

2. The apparatus of claim 1, wherein said plurality of porous frits are coaxially positioned with respect to one another, said one porous frit having a larger cross-section than said another porous frit, and additionally including a core member centrally located in said housing chamber, said core member being spaced from said another porous frit to define therebetween said outlet channel.

3. The apparatus of claim 2, wherein said core member is provided with a centrally located chamber at one end thereof and a plurality of spaced channels extending from said centrally located chamber to said outlet channel.

4. The apparatus of claim 1, wherein said distribution means is incorporated into said removable end section of said housing and includes a plurality of distribution channels connected to spaced points on said inlet channels to provide even distribution of associated material to said inlet channel.

5. The apparatus of claim 4, wherein said removable end section of said housing is provided with a centrally located chamber adapted to be connected to an associated supply of material to be separated in said apparatus, said plurality of distribution channels being connected at one end to said centrally located chamber and extending radially outward therefrom in spaced relation to one another.

6. The apparatus of claim 1, wherein said housing, said plurality of porous frits, and said core member are each of a cylindrical configuration, wherein said housing includes a cylindric body section and a pair of removable end sections, one of said pair of removable end sections containing said distribution means, said collector means being contained in said core member and another of said pair of removable end sections.

7. The apparatus of claim 1, wherein said body section of said housing is provided with an outwardly extending flange on each end thereof, said removable end sections being removably attached to said flanges, and sealing means positioned intermediate said flanges and said removable end sections.

8. The apparatus of claim 7, wherein said distribution means comprises a central opening in said one of said removable end sections, a plurality of spaced channels extending radially outward from said central opening, and a plurality of channels interconnecting said radially extending channels and said inlet channel.

9. The apparatus of claim 8, wherein said body section of said housing includes a plurality of L-shaped passages in fluid communication with said interconnecting channels in said removable end section and said inlet channels.

10. The apparatus of claim 6, wherein said core member includes an end section having a central opening, a plurality of channels extending radially outward from said central openings, and a plurality of interconnecting channels connecting said radially extending channels with said outlet channel.

11. The apparatus of claim 6, additionally including a pair of collar-like members located intermediate said plurality of cylindrical porous frits and intermediate said removable end sections of said housing and said bed of chromatographic separation material.

12. The apparatus of claim 1, wherein said housing is of a box-like configuration having a plurality of sides, a bottom, and a removable lid constituting said removable end section, a pair sides of said housing having a pair of spaced grooves therein, another pair of said housing sides being provided with a plurality of evenly spaced openings, said plurality of porous frits being supported in said pair of spaced grooves, said distributor means being connected to said spaced openings in a first of said another pair of said housing sides, said collector means being connected to said spaced openings in a second of said another pair of said housing sides.

13. The apparatus of claim 12, wherein said distributor means and said collector means each comprises a manifold secured to one of said sides of housing, said manifold including a pair of members, a first of said pair of members being a centrally located opening, a second of said pair of members being provided with an elongated slot and a pair of spaced openings, said housing side being provided with a pair of elongated slots having said plurality of evenly spaced openings therein, said second of said pair of members of said manifold being secured to said side of said housing over said pair of elongated slots, said first of said pair of members of said manifold being secured to said second of said pair of members over said elongated slot.

14. The apparatus of claim 12, wherein said distributor means and said collector means each comprises a manifold secured to one of said sides of housing, said manifold including a pair of members, a first of said pair of members being a centrally located opening, a second of said pair of members being provided with an elongated slot and a pair of spaced openings, said housing side being provided with a pair of elongated slots having said plurality of evenly spaced openings therein, said second of said pair of members of said manifold being secured to said side of said housing over said pair of elongated slots, said first of said pair of members of said manifold being secured to said second of said pair of members over said elongated slot.

15. The apparatus of claim 12, wherein each of said sides of said housing includes a flange, a sealing means located intermediate said housing lid and said flanges of said sides, and means for removably securing said lid to said sides of said housing.

16. The apparatus of claim 1, additionally including means for adjusting the height of said bed of chromatographic material.

17. The apparatus of claim 16, wherein said bed height adjusting means includes a movable member positioned at one end of said bed, and means for moving said movable member.

18. The apparatus of claim 17, wherein said means for moving said movable member includes:
a plurality of spaced tubes secured to said movable member,
a plurality of rods extending through said tubes and connected at one end to said movable member, said plurality of rods extending through said housing, and
means located externally of said housing for controlling the length of said rods within said housing, thereby moving said movable member and adjusting the height of said bed.

19. The apparatus of claim 18, wherein said distributor means includes:
a fluid distributor secured to said housing and adapted to receive fluid from an associated source,
a plurality of spaced flexible tubes connected at one end to said fluid distributor and connected at an opposite end to said movable member in a spaced relation to each other,
said movable means being provided with a plurality of spaced passage ways and in fluid communication with said plurality of flexible tubes and said inlet channel.

20. The apparatus of claim 16, wherein said collector means includes a core member having a longitudinally extending opening and a plurality of transverse openings in fluid communication with said longitudinally extending opening, said transverse opening being adapted to direct fluid components passing through one of said porous frits into said longitudinally extending opening, and said longitudinally extending opening being connected to direct fluid components externally of said housing.

21. The apparatus of claim 16, wherein said removable end section of said housing includes:
an end cap removably secured to a bed section of said housing,
a plate located intermediate said end cap and said body section of said housing and removably secured to said body section,
said plate being constructed to retain said means for adjusting the height of said bed.

22. An improved method for chromatographic separation of fluid components utilizing horizontal flows, comprising the steps of:
retaining a bed of chromatographic separation material between a pair of spaced longitudinally extending porous frits,
forming a fluid inlet channel adjacent to and extending along a longitudinal length of a first of the pair of porous frits,
forming a fluid component collection channel adjacent to and extending along a longitudinal length of a second of the porous frits,
providing a fluid inlet distribution means for directing fluid evenly into the fluid inlet channel across an adjacent longitudinal surface of the first of the porous frits,
providing collection means for directing fluid components from the collection channel, and
directing fluid to be separated into the inlet channel and through the pair of spaced frits and the bed of chromatographic material along a longitudinal length of the frits and the bed in a horizontal flow path into the collection channel.

23. The method of claim 22, wherein the step of providing the fluid inlet distribution means includes the step of:
forming a fluid distributor assembly having a plurality of fluid passages configured to deliver fluid to the inlet channel at spaced locations to provide even distribution of the fluid through the adjacent porous frit and associated chromatographic material.

24. The method of claim 22, additionally including the steps of:
forming the porous frits, bed of chromatographic separation material, fluid inlet channel, and fluid component collection channel in cylindrical configuration, and
positioning the fluid component collection channel radially inwardly from the fluid inlet channel.

25. The method of claim 24, wherein the steps of providing a fluid inlet distribution means is carried out by:
providing a housing in spaced relation around the first of the pair of porous frits to form the fluid inlet channel,
providing the housing with a removable end section, and
forming in the removable end section of the housing a fluid inlet chamber and a plurality of spaced radially extending fluid distributing channels connecting the fluid inlet chamber with the fluid inlet channel.

26. The method of claim 24, additionally including the steps of:
providing a cylindrical core member within the second of the pair of porous members and spaced therefrom for tne fluid component collection chamber, and
forming in one end of the core member a chamber and a plurality of fluid passages extending from the chamber to the fluid component collection channel.

27. The method of claim 22, additionally including the steps of:
providing a housing having a plurality of side members, a bottom member, and a removable lid member,
providing two of the side members with a pair of spaced grooves,
positioning the pair of porous frits in the pair of spaced grooves,
forming a plurality of spaced horizontal openings in two of the side members and at least one externally located elongated groove in each of the two side members so as to be in fluid communication with the plurality of spaced openings,
attaching the fluid inlet distribution means to one of the side members so as to be in fluid communication with the groove in the one of the two side members, and
attaching the collection means to another of the side members so as to be in fluid communication with the groove in the another of the two side members.

28. The method of claim 27, additionally including the step of forming a pair of spaced grooves in each of the bottom and lid members of the housing so as to be aligned with the spaced grooves in the two side members.

29. The method of claim 27, additionally including the step of forming each of the fluid distribution means and the collection means by:
   providing a pair of elongated members,
   forming a centrally located aperture in one of the elongated members,
   forming a pair of spaced apertures and an elongated groove in the other elongated member such that the spaced apertures are located in the elongated groove, and
   securing the pair of elongated members together and to one of the side members over the externally located groove therein.

30. The method of claim 27, additionally including the step of providing a sealing means between the removable lid member and adjacent portions of the plurality of side members.

31. The method of claim 22, additionally including the step of adjusting the height of the bed of chromatographic separation material.

32. The method of claim 31, wherein the step of adjusting the height of the bed is carried out by the steps of:
   providing a movable member adjacent one end of the bed, and
   moving the movable member to adjust the height of the bed.

* * * * *